(12) United States Patent
Shen

(10) Patent No.: US 11,583,234 B2
(45) Date of Patent: Feb. 21, 2023

(54) IMAGE RECONSTRUCTION

(71) Applicant: Neusoft Medical Systems Co., Ltd., Liaoning (CN)

(72) Inventor: Dawei Shen, Liaoning (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 179 days.

(21) Appl. No.: 17/143,845

(22) Filed: Jan. 7, 2021

(65) Prior Publication Data

US 2021/0204888 A1 Jul. 8, 2021

(30) Foreign Application Priority Data

Jan. 7, 2020 (CN) .......................... 202010015527.7

(51) Int. Cl.
*A61B 6/03* (2006.01)
*A61B 6/00* (2006.01)
*G06T 11/00* (2006.01)

(52) U.S. Cl.
CPC .............. *A61B 6/032* (2013.01); *A61B 6/481* (2013.01); *A61B 6/54* (2013.01); *G06T 11/003* (2013.01);
(Continued)

(58) Field of Classification Search
CPC . G06T 11/003; G06T 11/005; G06T 2210/41; G06T 1/20; G06T 7/0014; G06T 1/60; G06T 2207/10124; G06T 2207/20104; G06T 7/0012; G06T 11/008; G06T 11/006; G06T 5/005; G06T 2207/30048; G06T 2200/04; G06T 2207/30101; G06T 2207/30104; G06T 2207/20084; G06T 2207/10081; G06T 2211/424; G06T 2211/408; G06T 7/11;
(Continued)

(56) References Cited

U.S. PATENT DOCUMENTS

| 7,522,696 B2 | 4/2009 | Imai |
| 10,327,728 B2 * | 6/2019 | Yoda ........................ A61B 6/54 |

(Continued)

FOREIGN PATENT DOCUMENTS

| CN | 101049243 A | 10/2007 |
| CN | 107693038 A | 2/2018 |
| JP | H06125889 A | 5/1994 |

OTHER PUBLICATIONS

Office Action and Search Report in Chinese Application No. 202010015527.7, dated Oct. 19, 2022, 14 pages (with Machine/Partial Translation).

*Primary Examiner* — Irakli Kiknadze
(74) *Attorney, Agent, or Firm* — Fish & Richardson P.C.

(57) ABSTRACT

Methods, devices, electronic devices, apparatus, and systems for image reconstruction are provided. In one aspect, a method includes: obtaining first Computed Tomography (CT) data collected by a CT device performing a first contrast medium tracking scan on a target object based on a first reciprocating scanning sequence, obtaining second CT data by the CT device performing a second contrast medium tracking scan on the target object based on a second reciprocating scanning sequence in response to determining that a CT value in the first CT data exceeds a CT value threshold, and reconstructing CT images of the target object by using the first CT data and the second CT data respectively.

20 Claims, 2 Drawing Sheets

(52) U.S. Cl.
CPC ............... *A61B 6/469* (2013.01); *A61B 6/504* (2013.01); *A61B 6/563* (2013.01); *G06T 2210/41* (2013.01)

(58) Field of Classification Search
CPC ........... G06T 5/20; G06T 7/174; G06T 7/136; G06T 5/004; G06T 7/40; G06T 2207/30004; G06T 2211/404; A61B 6/481; A61B 6/032; A61B 6/54; A61B 6/5205; A61B 6/504; A61B 6/563; A61B 6/469; A61B 6/0407; A61B 6/40; A61B 6/4435; A61B 6/503; A61B 6/5217; A61B 6/505; A61B 6/56; A61B 5/055; A61B 5/72; A61B 6/545; A61B 6/542; A61B 6/488; A61B 6/4035; A61B 6/482; A61B 6/027; A61B 6/507; A61B 6/541; A61B 6/463; A61B 11/008; A61B 11/006; A61B 6/486; A61B 6/5235; A61B 6/5258; A61B 6/467; A61B 6/461; A61B 6/583; A61B 5/02007; G01N 23/046; G06V 10/25
USPC ............................................ 378/4, 8, 21, 62
See application file for complete search history.

(56) References Cited

U.S. PATENT DOCUMENTS

| | | | |
|---|---|---|---|
| 10,610,169 B2 * | 4/2020 | Korporaal | G06T 7/0016 |
| 11,202,613 B2 | 12/2021 | Li | |
| 2007/0230653 A1 * | 10/2007 | Okamoto | A61B 5/02007 378/8 |
| 2010/0195893 A1 * | 8/2010 | Fuchigami | A61B 5/02007 382/132 |
| 2016/0073997 A1 | 3/2016 | Yoda et al. | |
| 2016/0081643 A1 * | 3/2016 | Tsubota | G06T 11/005 378/16 |
| 2016/0296178 A1 | 10/2016 | Korporaal | |
| 2017/0311918 A1 * | 11/2017 | Qi | A61B 6/5235 |
| 2019/0192091 A1 * | 6/2019 | Lee | A61B 6/504 |

* cited by examiner

IMAGE RECONSTRUCTION

CROSS REFERENCE TO RELATED APPLICATIONS

The present disclosure claims priority to Chinese Patent Application No. 202010015527.7 filed on Jan. 7, 2020, the entire content of which is incorporated herein by reference.

TECHNICAL FIELD

The present disclosure relates to the field of medical imaging technologies, and in particular to Computed Tomography (CT) image reconstruction.

BACKGROUND

In medical activities, contrast medium tracking technology is usually adopted to realize three-dimensional reconstruction for a target object, for example, blood vessel in human body. Firstly, a tomography scan is performed on a to-be-examined region to obtain an image of a pilot film of the to-be-examined region, and then a scope of a region of interest is selected by a doctor in the pilot film and a threshold of a CT value is configured. After contrast medium is injected, several tomography scans are performed on the region of interest until the CT value exceeds the threshold. Subsequently, clinical scans are performed.

In the contrast medium tracking technology, the tomography scans are designed to monitor the CT value of the region of interest. Because the tomography scans are intermittent, to avoid affecting the quality of a reconstructed image, data collected during the tomography scans cannot be taken as basis for image reconstruction. These tomography scan processes compromise the efficiency of image reconstruction and exposes a patient to radiation that could have been avoided.

SUMMARY

The present disclosure provides methods, devices, systems and apparatus for image reconstruction, e.g., for CT image reconstruction.

In general, one innovative aspect of the subject matter described in the present disclosure can be embodied in methods that include the actions of image reconstruction, including: obtaining first Computed Tomography (CT) data collected by a CT device performing a first contrast medium tracking scan on a target object based on a first reciprocating scanning sequence; obtaining second CT data collected by the CT device performing a second contrast medium tracking scan on the target object based on a second reciprocating scanning sequence to collect second CT data in response to determining that a CT value in the first CT data exceeds a CT value threshold; and reconstructing CT images of the target object by using the first CT data and the second CT data, respectively.

Other embodiments of this aspect include corresponding computer systems, electronic devices, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination.

In some embodiments, the first reciprocating scanning sequence includes m scanning passes, and the second reciprocating scanning sequence includes n scanning passes, m and n being integers larger than 1. Each scanning pass of the first reciprocating scanning sequence and the second reciprocating scanning sequence includes a start position and an ending position for a scanning table carrying the target object to move during a contrast medium tracking scanning process in the scanning pass. In each of the first reciprocating scanning sequence and the second reciprocating scanning sequence, two adjacent passes have contrary start positions and ending positions for the scanning table.

In some embodiments, the actions further include: in response to determining that the CT value exceeds the CT value threshold during a contrast medium tracking scanning process of a k-th scanning pass of the first reciprocating scanning sequence, k being an integer and no larger than m, modifying a number of scanning passes of the second reciprocating scanning sequence from n to n+m−k; and providing the modified number of scanning passes to the CT device to perform the second contrast medium tracking scan on the target object based on the second reciprocating scanning sequence with the modified number of scanning passes.

In some embodiments, the actions further include: in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence, before obtaining the second CT data collected by the CT device performing the second contrast medium tracking scan on the target object based on the second reciprocating scanning sequence, controlling the CT device to stop performing the first contrast medium tracking scan on the target object based on the first reciprocating scanning sequence and controlling the CT device to move the scanning table to the start position of the first scanning pass of the second reciprocating scanning sequence.

In some embodiments, the actions further include: in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence, before obtaining the second CT data collected by the CT device performing the second contrast medium tracking scan on the target object based on the second reciprocating scanning sequence, controlling the CT device to perform the first contrast medium tracking scan of a (k+1)-th scanning pass of the first reciprocating scanning sequence to move the scanning table to the start position of the first scanning pass of the second reciprocating scanning sequence.

In some embodiments, the actions further include: modifying a number of scanning passes of the second reciprocating scanning sequence from n to n+m−k−1; and providing the modified number of scanning passes to the CT device to perform the second contrast medium tracking scan on the target object based on the second reciprocating scanning sequence with the modified number of scanning passes.

In some embodiments, the actions further include: in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence, before obtaining the second CT data collected by the CT device performing the second contrast medium tracking scan on the target object based on the second reciprocating scanning sequence, modifying the start position and the ending position of each scanning pass of the second reciprocating scanning sequence.

In some embodiments, the actions further include: before obtaining the first CT data collected by the CT device performing the first contrast medium tracking scan on the target object based on the first reciprocating scanning sequence, obtaining a pilot film of the subject based on reconstruction of data collected by the CT device performing a tomography scan on a subject containing the target object. The target object is determined in the pilot film.

In some embodiments, a number of scanning passes in the first reciprocating scanning sequence is determined based on historical scanning data.

In some embodiments, reconstructing the CT images of the target object by using the first CT data and the second CT data respectively includes: reconstructing the CT images of the target object in three dimensions by using the first CT data and the second CT data respectively based on a CT image reconstruction algorithm.

In some embodiments, each of the first reciprocating scanning sequence and the second reciprocating scanning sequence includes a four-dimensional (4D) helical scanning sequence.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
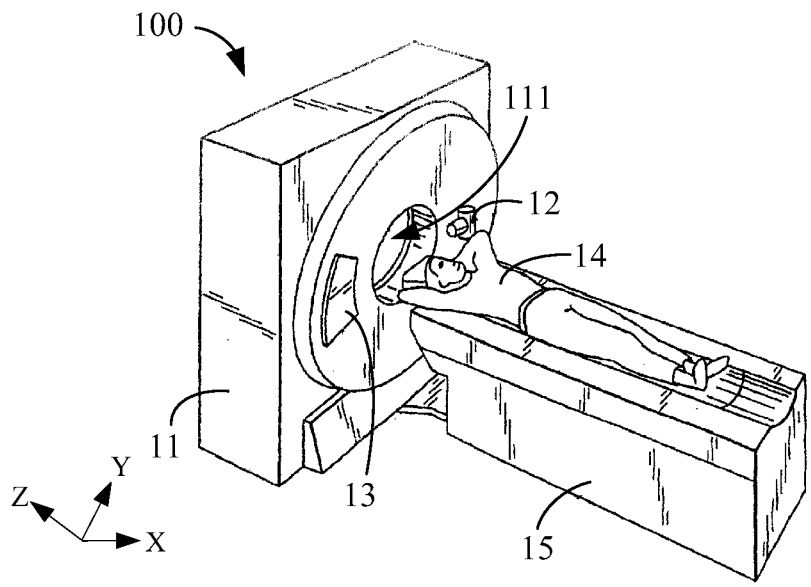
FIG. 1 is a structural schematic diagram of a CT device according to one or more examples of the present disclosure.

Examples will be described in detail herein, with the illustrations thereof represented in the drawings. When the following descriptions involve the drawings, like numerals in different drawings refer to like or similar elements unless otherwise indicated. The embodiments described in the following examples do not represent all embodiments consistent with the present disclosure. Rather, they are merely examples of apparatuses and methods consistent with some aspects of the present disclosure as detailed in the appended claims.

The terms used in the present disclosure are for the purpose of describing particular examples only, and are not intended to limit the present disclosure. Terms determined by "a", "the" and "said" in their singular forms in the present disclosure and the appended claims are also intended to include plurality, unless clearly indicated otherwise in the context. It should also be understood that the term "and/or" as used herein represents and includes any and all possible combinations of one or more of the associated listed items.

It is to be understood that, although the terms "first," "second," "third," and the like may be used in the present disclosure to describe various information, such information should not be limited to these terms. These terms are only used to distinguish one category of information from another. For example, without departing from the scope of the present disclosure, first information may be referred as second information; and similarly, the second information may also be referred as the first information. Depending on the context, the term "if" as used herein may be interpreted as "when" or "upon" or "in response to determining".

FIG. 1 is a structural schematic diagram of a CT device 100 according to an example of the present disclosure. The CT device 100 includes a scanning gantry 11, a radiation source 12, a detector 13, and a scanning table 15. The detector 13 may be an arc-shaped detector including a plurality of detector modules, and each detector module may include a sensor array. The scanning gantry 11 includes a bore (or an opening) 111 for accommodating a subject 14. The radiation source 12 and the detector 13 may be oppositely disposed inside the scanning gantry 11. The subject 14 injected with contrast medium, for example, a patient, is placed on the scanning table 15 which may bring the subject 14 to the bore 111. The radiation source 12 and the detector 13 are rotatable relative to the scanning gantry 12 and the subject 14.

In a scanning process, the radiation source 12 may produce an X ray beam with a strong penetrating force. The X ray beam is firstly collimated by a collimator and then passed through the subject 14 and then received by the detector 13. Due to different absorption capabilities of different tissues for X rays, information (CT data) of a slice may be obtained according to signals received by the detector 13. A data transmission system can be included in an electrical circuit interface between the detector 13 and an electronic device such as a computer. The data transmission system is used to process the CT data collected by the detector 13 and transmit the processed CT data to an image reconstruction system included in the electronic device for image reconstruction.

A CT data collection method provided by examples of the present disclosure will be detailed below in combination with the CT device 100 shown in FIG. 1.

Figure 2:
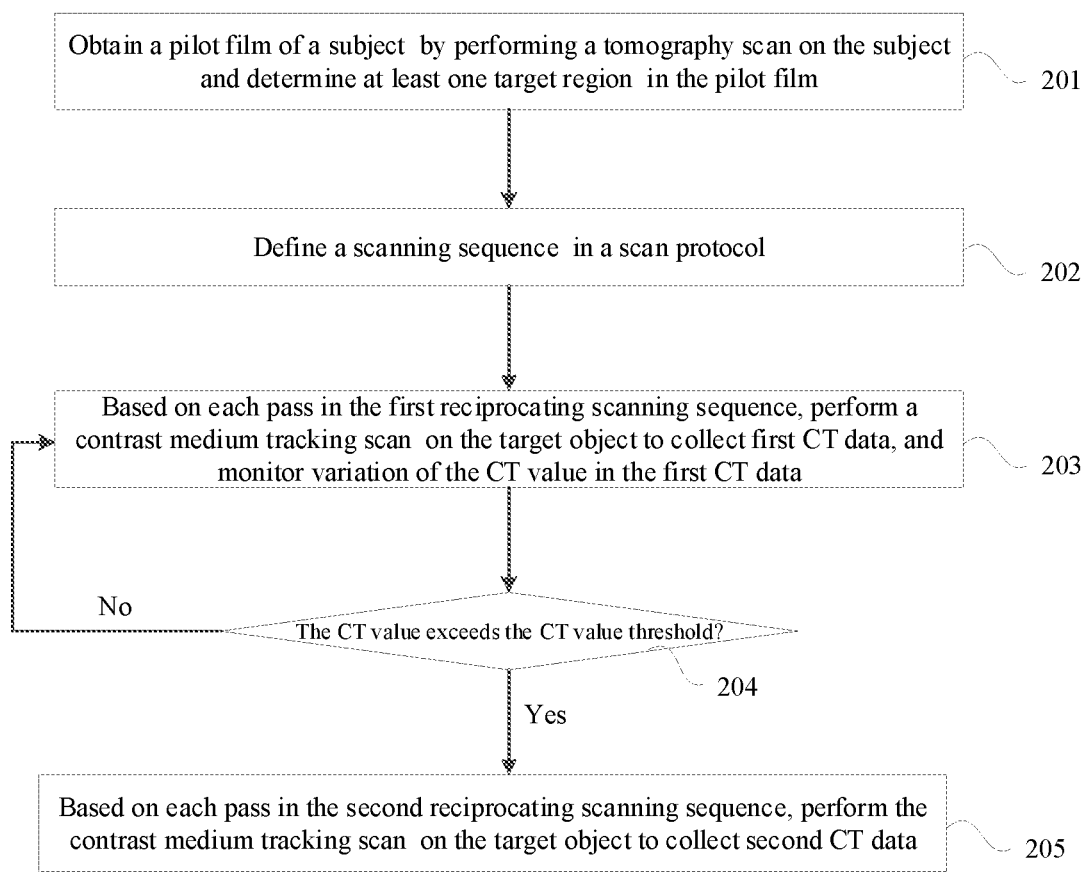
FIG. 2 is a flowchart of a CT data collection method according to one or more examples of the present disclosure.

FIG. 2 is a flowchart of a CT data collection method according to one or more examples of the present disclosure. The method includes the following steps.

At step 201, a pilot film of a subject is obtained by performing a tomography scan on the subject using the CT device 100 and at least one target region is determined in the pilot film.

The target region is a region of interest selected by a medical worker in the pilot film. In some examples, before a contrast medium is injected into the subject, a pilot film of the subject is obtained by performing a CT scan on the subject. After the target region is determined, the contrast medium is injected into the subject, and subsequent scans may be performed on the target region.

At step 202, a scanning sequence is defined in a scan protocol.

During execution of the scan protocol, a controller of the CT device 100 controls the scanning table 15, the radiation source 12, the detector 13, and the like to move, start or stop according to scanning parameters of the scanning sequence defined in the scanning protocol so as to realize collection of CT data. A control signal may be sent by an electronic device to the controller of the CT device 100 to perform the controlling.

The scanning sequence may include the following scanning parameters:

(1) a number of scanning passes, where a unidirectional scan performed on the target object is referred to as one pass, and the scanning sequence may include a plurality of passes;

(2) a start position and an ending position of each pass, which are used to represent a moving path of the scanning table 15 during a scanning process;

(3) a scanning time length of each pass;

(4) a scanning interval between adjacent passes; and (5) a scan preparation time length, which represents a preparation time length of the CT device 100 before starting scanning by using the scanning sequence, for example, a sum of a time length for distributing the scanning parameters to the scanning table 15 and a time length for the scanning table 15 to move to the start position of the first pass, and so on.

The target object is a particular region of the subject corresponding to the target region in the pilot film, for example, a heart or a brain or the like of the subject.

The scanning sequence can be a reciprocating scanning sequence. In the reciprocating scanning sequence, two adjacent passes are contrary in start positions and ending positions, for example, the start position and the ending position of the first pass are A and B respectively while the start position and the ending position of the second pass are B and A respectively. The start position and the ending position of a pass may be determined according to the target region in the pilot film.

In some examples of the present disclosure, because the CT value needs to be monitored, two reciprocating scanning sequences, i.e., a first reciprocating scanning sequence and a second reciprocating scanning sequence, are adopted to realize scanning. Each of the first reciprocating scanning sequence and the second reciprocating scanning sequence may include but not limited to a four-dimensional (4D) helical scanning sequence. The medical worker may configure scanning parameter values of the two scanning sequences respectively according to different subjects and image reconstruction requirements. The scanning parameter values of the two scanning sequences may be configured to be identical or different, which are defined in the scan protocol respectively.

In this example, if the medical worker only configures one original scanning sequence for the target object, the original scanning sequence may further be split into two scanning sequences which are then defined in the scan protocol. For example, an original scanning sequence configured by the medical worker is split into the first reciprocating scanning sequence with a number of passes being m and the second reciprocating scanning sequence with a number of passes being n, m and n being integers larger than 1, which are then defined in the scan protocol respectively. Other scanning parameter values of the two scanning sequences are identical.

In the two scanning sequences, because the first reciprocating scanning sequence is used to monitor the CT value, the value m may be configured based on historical scanning data so that m*t is greater than a time length for the contrast medium to reach the target object after the subject is injected with the contrast medium, where t represents a scanning time length of each pass. For example, it is assumed that the medical worker defines an original scanning sequence with the number of passes being 200 for brain, where the scanning time length of each pass is 1 second. It can be known from historical scanning data that the contrast medium reaches the target object, i.e., the brain, in 25 seconds after the subject is injected with contrast medium. In this case, m may be configured to be greater than 25, for example, to be 30, and n is configured to be 170. Thus, it can be determined that the CT value of the target object exceeds a CT value threshold before completing the scans of all the passes of the first reciprocating scanning sequence.

It is noted that step 202 is not limited to being performed after step 201, and may also be performed before step 201 or performed together with step 201.

After the subject 14 on the scanning table 15 is injected with the contrast medium, step 203 may be performed.

At step 203, based on each pass in the first reciprocating scanning sequence, a contrast medium tracking scan is performed by the CT device 100 on the target object to collect first CT data, and a variation of the CT value in the first CT data is monitored.

During the scanning process of each pass, the controller of the CT device 100, on the one hand, controls the scanning table 15 to move from the start position of the pass to the ending position, and on the other hand, controls the radiation source 12 to emit an X ray beam and controls the radiation source 12 and the detector 13 to rotate relative to the subject 14. During the scanning process, the detector 13 collects the CT data in real time and sends the CT data to an analog-to-digital (A/D) converter in the CT device 100 to calculate a corresponding CT value. The CT value is a corresponding value of each tissue in the CT data equivalent to an X ray attenuation coefficient.

At step 204, it is determined whether the CT value exceeds the CT value threshold during the scanning process of a k-th pass of the first reciprocating scanning sequence, k being an integer and no larger than m.

The CT device 100 monitors the variation of the CT value in real time and determines whether the CT value exceeds the CT value threshold. The CT value threshold may be configured by the medical worker according to actual requirements, that is, different CT value thresholds may be configured for different contrast media. The CT value threshold may be defined in the scan protocol together with the scanning parameters of the scanning sequence.

At step 204, if it is determined that the CT value is less than the CT value threshold during the scanning process of the k-th pass of the first reciprocating scanning sequence, the method returns to step 203, that is, the contrast medium tracking scan is continued for the target object based on a (k+1)-th pass of the first reciprocating scanning sequence, so as to monitor the variation of the CT value.

At step 204, if it is determined that the CT value is equal to or greater than the CT value threshold during the scanning process of the k-th pass of the first reciprocating scanning sequence, it indicates that the contrast medium reaches the target object, the contrast medium is sufficient, and the CT data collected afterwards can be used to reconstruct a high-quality CT image. After the scan of current pass ends, step 205 is performed. The CT device 100 may also record a moment when the CT value reaches the CT value threshold to distinguish data collected before the contrast medium is sufficient from data collected after the contrast medium is sufficient.

At step 205, based on each pass in the second reciprocating scanning sequence, the contrast medium tracking scan is performed by the CT device 100 on the target object to collect second CT data.

Similar to step 203, the contrast medium tracking scan is performed on the target object based on the second reciprocating scanning sequence, that is, the scan is performed based on each pass in the second reciprocating scanning sequence. During the scanning process, the controller of the CT device 100, on the one hand, controls the scanning table 15 to move from the start position of each pass to the ending position, and on the other hand, controls the radiation source 12 to emit an X ray beam and controls the radiation source 12 and the detector 13 to rotate relative to the subject. During the scanning process, the detector 13 collects the CT data in real time until the scan of each pass in the second reciprocating scanning sequence is completed.

In this example, after the scan protocol is executed, an entire scanning time length is expressed in the following formula (1):

$$T = T_{p1} + m^{*} + t_1 + \Sigma_{i=1}^{m-1} T_{mi} + T_{p2} + n^{*}t_2 + \Sigma_{j=1}^{n-1} T_{nj} \quad (1)$$

In the formula, T represents an entire scanning time length, $T_{p1}$ represents a scan preparation time length of the first reciprocating scanning sequence, m represents a planned number of passes in the first reciprocating scanning sequence, $t_1$ represents a scanning time length of each pass in the first reciprocating scanning sequence, $T_{mi}$ represents a scanning interval of two adjacent passes in the first reciprocating scanning sequence, $T_{p2}$ represents a scan preparation time length of the second reciprocating scanning sequence, n represents a planned number of passes in the second reciprocating scanning sequence, $t_2$ represents a scanning time length of each pass in the second reciprocating scanning sequence, $T_{nj}$ represents a scanning interval of two adjacent passes in the second reciprocating scanning sequence.

In this example, the entire scanning process is optimized so that the CT value tracking process for the region of interest is included in the process of data collection, thereby eliminating the need of spending additional time in monitoring the CT value, and improving the efficiency of data collection. Further, it is not required to perform a separate scan for monitoring the CT value for the patient, thereby decreasing the dose received by the patient. Further, because two scanning sequences are employed for scanning, the data collected before the contrast medium is sufficient and the data collected after the contrast medium is sufficient in the collected CT data can be distinguished.

In another example, since, when defining the scanning sequence, m*t in the first reciprocating scanning sequence is configured to be greater than a time length for the contrast medium to reach the target object after the subject is injected with the contrast medium, that is, when the CT value exceeds the CT value threshold, the scan of no more than all passes in the first reciprocating scanning sequence is performed. In this example, a number of undone passes in the first reciprocating scanning sequence are incorporated into the second reciprocating scanning sequence to ensure the collected CT data volume reaches the data volume require-ments of the medical worker. It is understood that the more the collected CT data volume is, the more accurate a CT image reconstructed with the collected CT data is.

Figure 3:
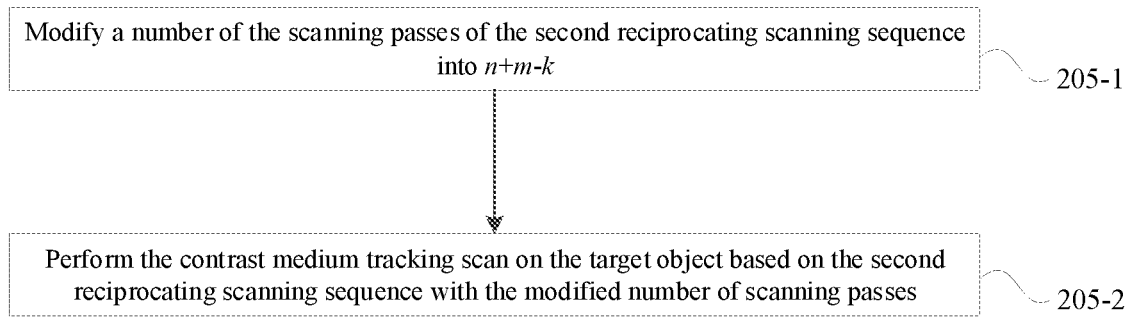
FIG. 3 is a specific flowchart of step 205 in FIG. 2.

If it is determined that the CT value exceeds the CT value threshold during a scanning process of the k-th (m≥k) scanning pass of the first reciprocating scanning sequence, step 205 includes the following steps as shown in FIG. 3.

At step 205-1, a number of the scanning passes of the second reciprocating scanning sequence is modified into n+m−k.

m represents a planned number of passes of the first reciprocating scanning sequence, and n represents a planned number of passes of the second reciprocating scanning sequence, m and n being integers larger than 1.

At step 205-2, the contrast medium tracking scan is performed on the target object based on the second reciprocating scanning sequence with the modified number of scanning passes.

After such modification, the total number of scanning passes is n+m, and the collected CT data volume can satisfy the anticipated data volume of the medical worker. The entire scanning time length is expressed in the following formula (2):

$$T = T_{p1} + k^{*} + t_1 + \Sigma_{i=1}^{k-1} T_{mi} + T_{p2}(n+m-k)^{*}t_2 + \Sigma_{j=1}^{n+m-k-1} T_{nj} \quad (2)$$

In this example, each of the first reciprocating scanning sequence and the second reciprocating scanning sequence is a 4D helical scanning sequence and the monitoring of the CT value is achieved through the first reciprocating scanning sequence. Therefore, compared with the monitoring of the CT value through tomography scans, the CT data collection method provided in the examples of the present disclosure can reduce the data collection time and improve the data collection efficiency on the precondition of the collected CT data volume satisfying the anticipated data volume of the medical worker.

If it is determined that the CT value exceeds the CT value threshold during the scanning process of the k-th scanning pass of the first reciprocating scanning sequence, because the reciprocating scanning sequence has directionality, that is, two adjacent passes are contrary in start positions and ending positions, it will be seen that the ending position of the k-th scanning pass is different from the start position of the first scanning pass of the second reciprocating scanning sequence. For example, the ending position of the k-th pass of the first reciprocating scanning sequence is B, that is, when the scan of the k-th pass is completed, the scanning table 15 is at the position B; the start position of the first pass of the second reciprocating scanning sequence is A, that is, the scanning table 15 is required to be located at the position A when the scan of the second reciprocating scanning sequence is started. In this case, it is required to solve the problem of position difference. Three possible processing manners are provided below.

Manner 1

If it is determined that the CT value is equal to or greater than the CT value threshold during the scanning process of the k-th pass of the first reciprocating scanning sequence at step 204, the contrast medium tracking scan performed on the target object based on the first reciprocating scanning sequence is stopped, and only the scanning table 15 is controlled to move to the start position of the first scanning pass of the second reciprocating scanning sequence. In this process, the radiation source 12 does not emit X rays and the detector 13 does not collect CT data until the scanning table 15 is located at the start position of the first scanning pass of the second reciprocating scanning sequence. At this time, the step 205 is performed to perform the contrast medium tracking scan on the target object based on each pass of the second reciprocating scanning sequence.

Manner 2

If it is determined that the CT value is equal to or greater than the CT value threshold during the scanning process of the k-th pass of the first reciprocating scanning sequence at step 204, the scan of the next pass of the first reciprocating scanning sequence is continued, that is, the scan of the (k+1)-th pass of the first reciprocating scanning sequence is performed to move the scanning table 15 to the start position of the first scanning pass of the second reciprocating scanning sequence. In this process, the radiation source 12 emits X rays and the detector 13 collects CT data. When the scan of the (k+1)-th pass is completed, the scanning table 15 is located at the start position of the first scanning pass of the second reciprocating scanning sequence. At this time, step 205 is performed to perform the contrast medium tracking scan on the target object based on each pass of the second reciprocating scanning sequence.

In this manner, the scan of an extra pass of the first reciprocating scanning sequence is performed, and therefore the modified number of the passes of the second reciprocating scanning sequence will further be decreased by 1 based on the above pass incorporation process, that is, the number of passes of the second reciprocating scanning sequence is modified into n+m−k−1. Thus, the total number of the passes in the two scanning sequences is n+m which is equal to the number planned by the medical worker.

Manner 3

If it is determined that the CT value is equal to or greater than the CT value threshold during the scanning process of the k-th pass of the first reciprocating scanning sequence at step 204, the start position and the ending position of each scanning pass of the second reciprocating scanning sequence in the scan protocol are modified, that is, the start position and the ending position of each scanning pass of the second reciprocating scanning sequence are reversed. For example, it is assumed that when the scan of the k-th pass is completed, the scanning table 15 is located at the position A, whereas the start position and the ending position of the first pass of the second reciprocating scanning sequence in the scan protocol are B and A respectively, and the start position and the ending position of the second pass are A and B respectively. In this case, the start position and the ending position of each pass in the second reciprocating scanning sequence in the scan protocol are reversed, that is, the start position and the ending position of the first pass are modified into A and B respectively, and the start position and the ending position of the second pass are modified into B and A respectively and so on.

If the CT value threshold is configured appropriately, the monitored CT value can exceed the CT value threshold before/when the scan of all scanning passes of the first reciprocating scanning sequence is completed. If the CT value threshold is configured inappropriately, e.g., too large, the second reciprocating scanning sequence may be manually triggered before the scan of all scanning passes of the first reciprocating scanning sequence is completed. In another example, after the scan of all scanning passes of the first reciprocating scanning sequence is completed, if the CT value is still not greater than the CT value threshold, the scan of the second reciprocating scanning sequence is also automatically triggered except that the data collected before the contrast medium is sufficient and the data collected after the contrast medium is sufficient in the collected CT data cannot be distinguished.

The examples of the present disclosure further provide an image reconstruction method. The image reconstruction method includes the following steps: CT data of the target object is collected using the CT data collection method in any above example, the CT data contains first CT data collected before the contrast medium is sufficient and second CT data collected after the contrast medium is sufficient; CT images of the target object are reconstructed by using the first CT data and the second CT data, respectively. By comparing a CT image of the target object reconstructed by using the first CT data with a CT image of the target object reconstructed by using the second CT data, it is possible to diagnose the exterior and interior of the target object (e.g., a blood vessel), for example, to diagnose the presence of a blood clot inside a blood vessel. In this scenario, the CT image reconstructed by using the first CT data collected before the contrast medium is sufficient can show whether the exterior of the vessel (e.g., the thickness of the outer wall of the vessel) is normal, while the CT image reconstructed by using the second CT data collected after the contrast medium is sufficient can show whether the interior of the vessel is normal. Since the CT values monitored under X-ray irradiation when the contrast medium is sufficient are significantly different from those when the contrast medium is insufficient, the position of the contrast medium passing inside the vessel can reflect the actual thickness inside the vessel, and thus the internal condition of the vessel can be determined. Reconstructing the CT images of the target object by using the first CT data and the second CT data respectively may include: reconstructing the CT images of the target object in three dimensions by using the first CT data and the second CT data respectively based on a CT image reconstruction algorithm.

Corresponding to the examples of the above CT data collection method and the above image reconstruction method, the present disclosure further provides an example of an electronic device.

Figure 4:
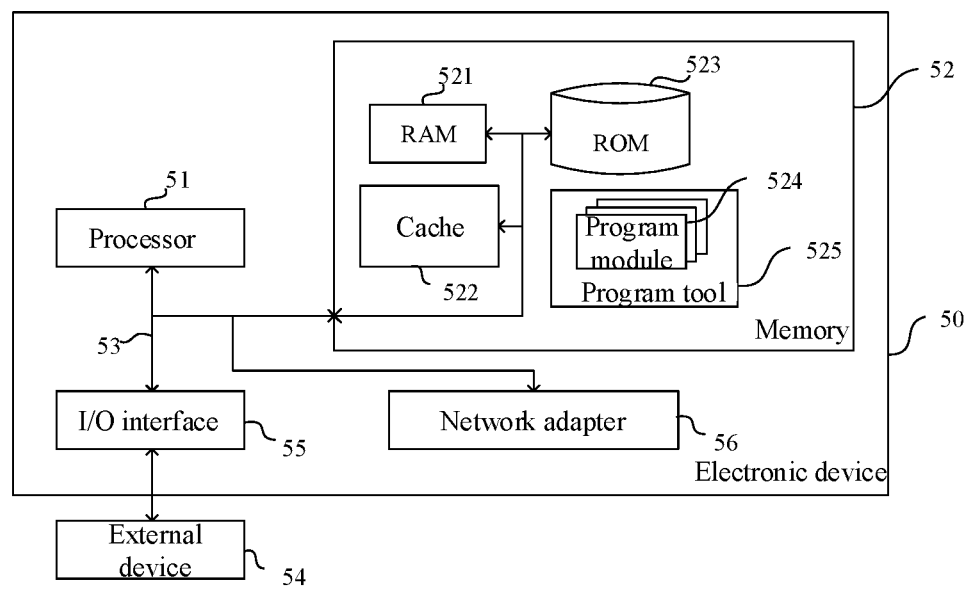
FIG. 4 is a structural schematic diagram of an electronic device according to one or more examples of the present disclosure.

FIG. 4 is a structural schematic diagram of an electronic device according to an example of the present disclosure, which shows a block diagram of an exemplary electronic device 50 suitable for realizing the examples of the present disclosure. The electronic device 50 in FIG. 4 is merely one example, and shall not bring any limitation to the function and use scope of the examples of the present disclosure. The electronic device 50 can be in communication with a CT device, e.g., the CT device 100 of FIG. 1.

As shown in FIG. 4, the electronic device 50 may be implemented in the form of a general computing device, for example, may be a server device. The components of the electronic device 50 include but not limited to: at least one processor 51, at least one memory 52, and a bus 53 connecting different system components (including memory 52 and processor 51).

The bus 53 includes a data bus, an address bus and a control bus.

The memory 52 may include a volatile memory such as a random access memory (RAM) 521 and/or a cache 522, and may further include a read only memory (ROM) 521.

The memory 52 may also include a program tool 525 (utility tool) with a group (at least one) of program modules 524. Such program module 524 includes but not limited to: an operating system, one or more application programs, other program modules, and program data. One or combination of these examples may include realization of network environment.

By running the computer programs stored on the memory 52, the processor 51 performs the following operations: obtaining the first CT data collected by the CT device by performing contrast medium tracking scan on the target object based on the first reciprocating scanning sequence; if it is determined that the CT value in the first CT data exceeds the CT value threshold, obtaining the second CT data collected by the CT device by performing contrast medium tracking scan on the target object based on the second reciprocating scanning sequence; and reconstructing CT images of the target object by using the first CT data and the second CT data respectively.

In some examples, the first reciprocating scanning sequence includes: m scanning passes; the second reciprocating scanning sequence includes n scanning passes, m and n being integers larger than 1; if it is determined that the CT value exceeds the CT value threshold during the scanning process of a k-th scanning pass of the first reciprocating scanning sequence, k being an integer and no larger than m, obtaining the second CT data collected by the CT device by performing contrast medium tracking scan on the target object based on the second reciprocating scanning sequence includes: modifying the number of the scanning passes of the second reciprocating scanning sequence from n to n+m−k; obtaining the second CT data collected by the CT device by performing contrast medium tracking scan on the target object based on the second reciprocating scanning sequence with the modified number of scanning passes.

In some examples, each scanning pass of the first reciprocating scanning sequence and the second reciprocating scanning sequence includes: a start position and an ending position for the scanning table carrying the target object to move during a contrast medium tracking scanning process. It is assumed that it is determined that the CT value exceeds the CT value threshold during a scanning process of a k-th scanning pass of the first reciprocating scanning sequence, k being an integer and no larger than m, and that an ending position of the k-th scanning pass is different from a start position of a first scanning pass of the second reciprocating scanning sequence. In this case, before obtaining the second CT data collected by the CT device by performing contrast medium tracking scan on the target object based on the second reciprocating scanning sequence, the operation further includes: controlling the CT device to stop performing contrast medium tracking scan on the target object based on the first reciprocating scanning sequence, and controlling the scanning table to move to the start position of the first scanning pass of the second reciprocating scanning sequence.

In some examples, each scanning pass of the first reciprocating scanning sequence and the second reciprocating scanning sequence includes: a start position and an ending position for the scanning table carrying the target object to move during a contrast medium tracking scanning process. It is assumed that it is determined that the CT value exceeds the CT value threshold during a scanning process of a k-th scanning pass of the first reciprocating scanning sequence, k being an integer and no larger than m, and that an ending position of the k-th scanning pass is different from a start position of a first scanning pass of the second reciprocating scanning sequence. In this case, before obtaining the second CT data collected by the CT device by performing contrast medium tracking scan on the target object based on the second reciprocating scanning sequence, the operation further includes: controlling the CT device to perform the scan of the (k+1)-th scanning pass of the first reciprocating scanning sequence, and controlling the scanning table to move to the start position of the first scanning pass of the second reciprocating scanning sequence.

In some examples, the first reciprocating scanning sequence includes: m scanning passes; the second reciprocating scanning sequence includes n scanning passes, m and n being integers larger than 1; obtaining the second CT data collected by the CT device by performing contrast medium tracking scan on the target object based on the second reciprocating scanning sequence includes: modifying the number of the scanning passes of the second reciprocating scanning sequence from n to n+m−k−1; and obtaining the second CT data collected by the CT device by performing contrast medium tracking scan on the target object based on the second reciprocating scanning sequence with the modified number of scanning passes.

In some examples, each scanning pass of the first reciprocating scanning sequence and the second reciprocating scanning sequence includes: a start position and an ending position for the scanning table carrying the target object to move during a contrast medium tracking scanning process. It is assumed that it is determined that the CT value exceeds the CT value threshold during a scanning process of a k-th scanning pass of the first reciprocating scanning sequence, k being an integer and no larger than m, and an ending position of the k-th scanning pass is different from a start position of a first scanning pass of the second reciprocating scanning sequence. In this case, before obtaining the second CT data collected by the CT device by performing contrast medium tracking scan on the target object based on the second reciprocating scanning sequence, the operation further includes: modifying the start position and the ending position of each scanning pass of the second reciprocating scanning sequence.

In some examples, the operation further includes: before performing the first contrast medium tracking scan on the target object based on the first reciprocating scanning sequence, obtaining a pilot film of the target object, where the pilot film is obtained based on reconstruction of the data obtained by performing a tomography scan on a subject containing the target object using the CT device; and determining the target object in the pilot film.

In some examples, the operation further includes: determining a number of scanning passes in the first reciprocating scanning sequence based on historical scanning data.

In some examples, reconstructing the CT images of the target object by using the first CT data and the second CT data respectively includes: reconstructing the CT images of the target object in three dimensions by using the first CT data and the second CT data respectively based on a CT image reconstruction algorithm.

In some examples, each of the first reciprocating scanning sequence and the second reciprocating scanning sequence include a 4D helical scanning sequence.

The electronic device 50 may also communicate with one or more external devices 54 (for example, keyboard, pointing device, CT device 100 and the like) through an input/output (I/O) interface 55. Further, the electronic device 50 may also communicate with one or more networks (for example, local area network (LAN), wide area network (WAN) and/or public network, e.g. internet) through a network adapter 56. As shown in FIG. 4, the network adapter 56 may communicate with other modules of the electronic device 50 generated by model through a bus 53. It is understood that other hardware and/or software modules may be used in combination with the model-generated electronic device 50 in spite of not being shown in FIG. 4, including but not limited to microcodes, device driver, redundant processor, external magnetic disk drive array, Redundant Arrays of Independent Disk (RAID) system, magnetic tape driver and data backup storage system and so on.

The foregoing disclosure is merely illustrative of some examples of the present disclosure but not intended to limit the present disclosure, and any modifications, equivalent substitutions, adaptations thereof made within the spirit and principles of the disclosure shall be encompassed in the scope of protection of the present disclosure.

What is claimed is:

1. An image reconstruction method, comprising:
   obtaining first Computed Tomography (CT) data collected by a CT device performing a first contrast medium tracking scan on a target object based on a first reciprocating scanning sequence;
   obtaining second CT data collected by the CT device performing a second contrast medium tracking scan on the target object based on a second reciprocating scanning sequence to collect second CT data in response to determining that a CT value in the first CT data exceeds a CT value threshold; and
   reconstructing CT images of the target object by using the first CT data and the second CT data, respectively,
   wherein the first reciprocating scanning sequence comprises m scanning passes, and the second reciprocating scanning sequence comprises n scanning passes, m and n being integers larger than 1,
   wherein each scanning pass of the first reciprocating scanning sequence and the second reciprocating scanning sequence comprises: a start position and an ending position for a scanning table carrying the target object to move during a contrast medium tracking scanning process in the scanning pass, and
   wherein, in each of the first reciprocating scanning sequence and the second reciprocating scanning sequence, two adjacent passes have contrary start positions and ending positions for the scanning table.

2. The method according to claim 1, further comprising:
   in response to determining that the CT value exceeds the CT value threshold during a contrast medium tracking scanning process of a k-th scanning pass of the first reciprocating scanning sequence, k being an integer and no larger than m,
   modifying a number of scanning passes of the second reciprocating scanning sequence from n to n+m−k; and
   providing the modified number of scanning passes to the CT device to perform the second contrast medium tracking scan on the target object based on the second reciprocating scanning sequence with the modified number of scanning passes.

3. The method according to claim 1, further comprising:
   in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence,
   before obtaining the second CT data collected by the CT device performing the second contrast medium tracking scan on the target object based on the second reciprocating scanning sequence, controlling the CT device to stop performing the first contrast medium tracking scan on the target object based on the first reciprocating scanning sequence and controlling the CT device to move the scanning table to the start position of the first scanning pass of the second reciprocating scanning sequence.

4. The method according to claim 1, further comprising:
   in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence,
   before obtaining the second CT data collected by the CT device performing the second contrast medium tracking scan on the target object based on the second reciprocating scanning sequence, controlling the CT device to perform the first contrast medium tracking scan of a (k+1)-th scanning pass of the first reciprocating scanning sequence to move the scanning table to the start position of the first scanning pass of the second reciprocating scanning sequence.

5. The method according to claim 4, further comprising:
   modifying a number of scanning passes of the second reciprocating scanning sequence from n to n+m−k−1; and
   providing the modified number of scanning passes to the CT device to perform the second contrast medium tracking scan on the target object based on the second reciprocating scanning sequence with the modified number of scanning passes.

6. The method according to claim 1, further comprising:
   in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence,
   before obtaining the second CT data collected by the CT device performing the second contrast medium tracking scan on the target object based on the second reciprocating scanning sequence, modifying the start position and the ending position of each scanning pass of the second reciprocating scanning sequence.

7. The method according to claim 1, further comprising:
   before obtaining the first CT data collected by the CT device performing the first contrast medium tracking scan on the target object based on the first reciprocating scanning sequence, obtaining a pilot film of a subject based on reconstruction of data collected by the CT device performing a tomography scan on the subject, the subject containing the target object, wherein the target object is determined in the pilot film.

8. The method according to claim 1, wherein a number of scanning passes in the first reciprocating scanning sequence is determined based on historical scanning data.

9. The method according to claim 1, wherein reconstructing the CT images of the target object by using the first CT data and the second CT data respectively comprises:

reconstructing the CT images of the target object in three dimensions by using the first CT data and the second CT data respectively based on a CT image reconstruction algorithm.

10. The method according to claim 1, wherein each of the first reciprocating scanning sequence and the second reciprocating scanning sequence comprises a four-dimensional (4D) helical scanning sequence.

11. An electronic device, comprising:
at least one processor; and
a non-transitory computer-readable storage medium coupled to the at least one processor and storing programming instructions for execution by the at least one processor, wherein the programming instructions instruct the at least one processor to perform operations for image reconstruction, the operations comprising:
obtaining first Computed Tomography (CT) data collected by a CT device performing a first contrast medium tracking scan on a target object based on a first reciprocating scanning sequence;
obtaining second CT data collected by a CT device performing a second contrast medium tracking scan on the target object based on a second reciprocating scanning sequence in response to determining that a CT value in the first CT data exceeds a CT value threshold; and
reconstructing CT images of the target object by using the first CT data and the second CT data respectively,
wherein the first reciprocating scanning sequence comprises m scanning passes, and the second reciprocating scanning sequence comprises n scanning passes, m and n being integers larger than 1,
wherein each scanning pass of the first reciprocating scanning sequence and the second reciprocating scanning sequence comprises: a start position and an ending position for a scanning table carrying the target object to move during a contrast medium tracking scanning process in the scanning pass, and
wherein, in each of the first reciprocating scanning sequence and the second reciprocating scanning sequence, two adjacent passes have contrary start positions and ending positions for the scanning table.

12. The electronic device according to claim 11, wherein the operations further comprise:
in response to determining that the CT value exceeds the CT value threshold during a contrast medium tracking scanning process of a k-th scanning pass of the first reciprocating scanning sequence, k being an integer and no larger than m,
modifying a number of scanning passes of the second reciprocating scanning sequence from n to n+m−k; and
providing the modified number of scanning passes to the CT device to perform the second contrast medium tracking scan on the target object based on the second reciprocating scanning sequence with the modified number of scanning passes.

13. The electronic device according to claim 11, wherein the operations further comprise:
in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence,
before obtaining the second CT data collected by performing the second contrast medium tracking scan on the target object using the CT device based on the second reciprocating scanning sequence, controlling the CT device to stop performing the first contrast medium tracking scan on the target object based on the first reciprocating scanning sequence and controlling the CT device to move the scanning table to the start position of the first scanning pass of the second reciprocating scanning sequence.

14. The electronic device according to claim 11, wherein the operations further comprise:
in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence,
before obtaining the second CT data collected by the CT device performing the second contrast medium tracking scan on the target object based on the second reciprocating scanning sequence, controlling the CT device to perform the first contrast medium tracking scan of a (k+1)-th scanning pass of the first reciprocating scanning sequence to move the scanning table to the start position of the first scanning pass of the second reciprocating scanning sequence.

15. The electronic device according to claim 14, wherein the operations further comprise:
modifying a number of scanning passes of the second reciprocating scanning sequence from n to n+m−k−1; and
providing the modified number of scanning passes to the CT device to perform the second contrast medium tracking scan on the target object based on the second reciprocating scanning sequence with the modified number of scanning passes.

16. The electronic device according to claim 11, wherein the operations further comprise:
in response to determining that the CT value exceeds the CT value threshold during a contrast medium tracking scanning process of a k-th scanning pass of the first reciprocating scanning sequence, k being an integer and no larger than m, and that an ending position of the k-th scanning pass is different from a start position of a first scanning pass of the second reciprocating scanning sequence,
before obtaining the second CT data collected by the CT device performing the second contrast medium tracking scan on the target object based on the second reciprocating scanning sequence, modifying the start position and the ending position of each scanning pass of the second reciprocating scanning sequence.

17. The electronic device according to claim 11, wherein the operations further comprise:
before obtaining the first CT data collected by the CT device performing the first contrast medium tracking scan on the target object based on the first reciprocating scanning sequence, obtaining a pilot film of a subject based on reconstruction of data collected by the CT device performing a tomography scan on the subject, the subject containing the target object, wherein the target object is determined in the pilot film.

18. The electronic device according to claim 11, wherein reconstructing the CT images of the target object by using the first CT data and the second CT data respectively comprises:
reconstructing the CT images of the target object in three dimensions by using the first CT data and the second CT data respectively based on a CT image reconstruction algorithm.

19. A non-transitory computer-readable storage medium storing programming instructions for execution by at least one processor to perform operations for image reconstruction, the operations comprising:
obtaining first Computed Tomography (CT) data collected by a CT device performing a first contrast medium tracking scan on a target object based on a first reciprocating scanning sequence;
obtaining second CT data collected by a CT device performing a second contrast medium tracking scan on the target object based on a second reciprocating scanning sequence in response to determining that a CT value in the first CT data exceeds a CT value threshold; and
reconstructing CT images of the target object by using the first CT data and the second CT data respectively,
wherein the first reciprocating scanning sequence comprises m scanning passes, and the second reciprocating scanning sequence comprises n scanning passes, m and n being integers larger than 1,
wherein each scanning pass of the first reciprocating scanning sequence and the second reciprocating scanning sequence comprises: a start position and an ending position for a scanning table carrying the target object to move during a contrast medium tracking scanning process in the scanning pass, and
wherein, in each of the first reciprocating scanning sequence and the second reciprocating scanning sequence, two adjacent passes have contrary start positions and ending positions for the scanning table.

20. The non-transitory computer-readable storage medium according to claim 19, wherein the operations further comprise:
before obtaining the first CT data collected by the CT device performing the first contrast medium tracking scan on the target object based on the first reciprocating scanning sequence, obtaining a pilot film of a subject based on reconstruction of data collected by the CT device performing a tomography scan on the subject, the subject containing the target object, wherein the target object is determined in the pilot film.

* * * * *